United States Patent
Beev et al.

(10) Patent No.: US 9,788,726 B2
(45) Date of Patent: Oct. 17, 2017

(54) DEVICE AND METHOD FOR MEASURING VIBRATION TRANSMITTANCE OF STERNUM

(75) Inventors: Nikolai Beev, Espoo (FI); Juha Hautalahti, Tampere (FI); Jari Laurikka, Lempäälä (FI); Matti Tarkka, Tampere (FI); Jari Hyttinen, Tampere (FI)

(73) Assignee: TAYS SYDÄNKESKUS OY, Tampere (FI)

( * ) Notice: Subject to any disclaimer, the term of this patent is extended or adjusted under 35 U.S.C. 154(b) by 319 days.

(21) Appl. No.: 14/123,762

(22) PCT Filed: Jun. 9, 2011

(86) PCT No.: PCT/FI2011/050543
§ 371 (c)(1),
(2), (4) Date: Feb. 21, 2014

(87) PCT Pub. No.: WO2012/168534
PCT Pub. Date: Dec. 13, 2012

(65) Prior Publication Data
US 2014/0228703 A1    Aug. 14, 2014

(51) Int. Cl.
*A61B 5/00* (2006.01)

(52) U.S. Cl.
CPC .......... *A61B 5/0051* (2013.01); *A61B 5/4504* (2013.01); *A61B 5/4538* (2013.01); *A61B 5/6823* (2013.01)

(58) Field of Classification Search
CPC .............................. A61B 5/0051; A61B 5/4504
See application file for complete search history.

(56) References Cited

U.S. PATENT DOCUMENTS

| 3,477,422 A | 11/1969 | Jurist, Jr. et al. |
| 4,754,763 A | 7/1988 | Doemland |
| (Continued) | | |

FOREIGN PATENT DOCUMENTS

| GB | 2156983 A | 10/1985 |
| RU | 19361 U1 | 8/2001 |
| (Continued) | | |

OTHER PUBLICATIONS

El-Ansary, Doa, Gordon Waddington, and Roger Adams. "Measurement of non-physiological movement in sternal instability by ultrasound." The Annals of thoracic surgery 83.4 (2007): 1513-1516.*

(Continued)

*Primary Examiner* — Michael C Stout
*Assistant Examiner* — Nicholas E Kolderman
(74) *Attorney, Agent, or Firm* — Ziegler IP Law Group, LLC

(57) ABSTRACT

A method for measuring vibration transmittance of a sternum noninvasively includes producing vibration, transmitting the vibration to a first side the sternum through skin and soft tissues, obtaining response data of the sternum from a second side of the sternum through skin and soft tissues, which first and second sides of the sternum are on different sides of the midline of the sternum, and processing said response data for determining transmittance of vibration of the sternum. The response data may be used for defining state of a patient such as sternal instability of the breastbone or abnormal healing in the sternum after open chest surgery by surgeons.

17 Claims, 3 Drawing Sheets

(56) References Cited

U.S. PATENT DOCUMENTS

| | | | |
|---|---|---|---|
| 4,989,613 A | | 2/1991 | Finkenberg |
| 5,006,984 A | * | 4/1991 | Steele ................... A61B 5/417 600/587 |
| 5,024,239 A | * | 6/1991 | Rosenstein .......... A61B 5/0051 600/552 |
| 5,368,044 A | * | 11/1994 | Cain .................... A61B 5/4504 600/552 |
| 5,784,478 A | | 7/1998 | Untersander |
| 2002/0143268 A1 | | 10/2002 | Meredith |
| 2005/0113691 A1 | * | 5/2005 | Liebschner .......... A61B 5/4504 600/437 |
| 2009/0148811 A1 | | 6/2009 | Pan |
| 2009/0264754 A1 | * | 10/2009 | Dahl ....................... A61B 8/44 600/438 |

FOREIGN PATENT DOCUMENTS

WO 90/06720 A1 6/1990
WO 91/06245 A1 5/1991

OTHER PUBLICATIONS

Rendon, David, et al., "Mapping the Human Body for Vibrations using an Accelerometer", Proceedings of 29th Annual International Conference of the IEEE on Engineering in Medicine and Biology Society, Aug. 23-26, 2007, pp. 1671-1674.

El-Ansary, Doa, et al., "Measurement of Non-Physiological Movement in Sternal Instability by Ultrasound", The Society of Thoracic Surgeons, vol. 83, Issue 4, Oct. 23, 2006, pp. 1513-1516.

Extended European Search Report received for European Patent Application No. EP11867251.8, dated Feb. 10, 2015, 11 pages.

Decision on Grant of a Patent of Invention, Russia Federal Service on Industrial Property, Patents, and Trade Marks, Applicatin No. 2013158188, Jul. 13, 2016, 7 pages.

* cited by examiner

DEVICE AND METHOD FOR MEASURING VIBRATION TRANSMITTANCE OF STERNUM

FIELD OF THE INVENTION

The present invention relates to a device and a method for measuring vibration transmittance of a sternum.

BACKGROUND OF THE INVENTION

Sternal instability is an abnormal motion of the breastbone after open chest surgery. Detection of sternal instability is complex, because it is an abnormal condition that is obscured and manifests itself differently in each case. Surgeons rely primarily on manual examination techniques, such as palpation. In palpation regional tenderness and motion between sternal halves is estimated manually. However, this evaluation is subjective, essentially qualitative and prone to errors. In addition, imaging methods such as chest X-ray and computerized tomography, CT, are used for defining bone separation and fragmentation, but they may fail to indicate small movements of the sternal halves when they are still tightly held together. In addition, X-ray and CT devices are not available everywhere, radiation of X-ray device is not suitable to be used frequently and CT is a quite expensive solution for defining sternal instability. X-ray may also indicate that the sternum is in two parts, even if it is already in one part.

There is, therefore, a need for a noninvasive solution that defines sternal stability in a reliable, accurate and objective way. This kind of solution gives doctors measurement data about the state of the sternum. The doctors may use this data for prescribing of the most suitable treatment that could range from conservative monitoring and advice on daily routine activities to invasive revision of the operation.

SUMMARY OF THE INVENTION

Now there has been invented a method and technical equipment implementing the method, by which the above problems are alleviated. Various aspects of the invention include a method and an apparatus, which are characterized by what is stated in the independent claims. Various embodiments of the invention are disclosed in the dependent claims.

The invention relates to measuring vibration transmittance of a sternum noninvasively as well as a measuring system and a device.

Vibration is produced, for example by a specific device suitable for this purpose. The produced vibration is transmitted for example by a transmitting means such as a transmitter, to a first side of the sternum through skin and soft tissues. The transmitted vibration is then obtained, for example by a sensing means such as a sensor, as response data of the sternum from a second side of the sternum through skin and soft tissues. The first and the second sides of the sternum are on opposite sides of the midline of the sternum. Response data is then processed, for example by the same specific device that produced the vibration or by a computer, for determining transmittance of vibration of the sternum.

According to a first aspect of the invention, there is provided a method for measuring vibration transmittance of a sternum noninvasively, the method comprising producing vibration, transmitting the vibration to a first side of the sternum through skin and soft tissues, obtaining response data of the sternum from a second side of the sternum through skin and soft tissues, which first and second sides of the sternum are on opposite sides of the midline of the sternum, and processing said response data for determining transmittance of vibration of the sternum.

According to an embodiment, the spectral content of the produced vibration is in the 50-1500 Hz range. According to an embodiment, the spectral content of the produced vibration spectral content of the produced controlled vibration is in the 50-2000 Hz range. According to an embodiment, the processing comprises producing a transfer function from response data and extracting parameters from the transfer function. According to an embodiment the measuring of vibration transmittance of the sternum is performed at least twice, wherein the first measuring is executed before a sternal incision of the sternum and the second measuring is executed after the sternal incision of the sternum, and wherein the response data of the first and second measurements are compared. According to an embodiment the measuring of vibration transmittance of the sternum is executed to the sternum at least at two different positions.

According to a second aspect of the invention, there is provided a system for measuring vibration transmittance of a sternum noninvasively, wherein the system comprises a device comprising a processor and a memory including computer program code for producing vibration, a transmitter for transmitting the vibration to a first side of the sternum through skin and soft tissues, a sensor for obtaining response data of the sternum from a second side of the sternum through skin and soft tissues, which first and second sides of the sternum are on opposite sides of the midline of the sternum and wherein the device is further arranged to process said response data for determining transmittance of vibration of the sternum.

According to an embodiment, the device of the system is further arranged to receive said obtained data for further data processing. According to an embodiment, the sensor is connected to a computer that is arranged to receive said obtained data for further data processing. According to an embodiment, wherein the transmitter of the system is a vibration actuator. According to an embodiment, wherein the sensor is an accelerometer. According to an embodiment, wherein the transmitter and the sensor are connected to each other by a haft.

According to a third aspect of the invention, there is provided a device for measuring sternal vibration transmittance of a sternum noninvasively, the device comprising means for generating vibration, means for transmitting the vibration to a first side of the sternum through skin and soft tissue, means for obtaining response data of the sternum from a second side of the sternum through skin and soft tissue, which first and second sides of the sternum are on opposite sides of the midline of the sternum, and means for processing said response data for determining transmittance of vibration of the sternum.

DESCRIPTION OF THE DRAWINGS

In the following, various embodiments of the invention will be described in more detail with reference to the appended drawings, in which.

DETAILED DESCRIPTION OF THE EMBODIMENTS

Figure 1:
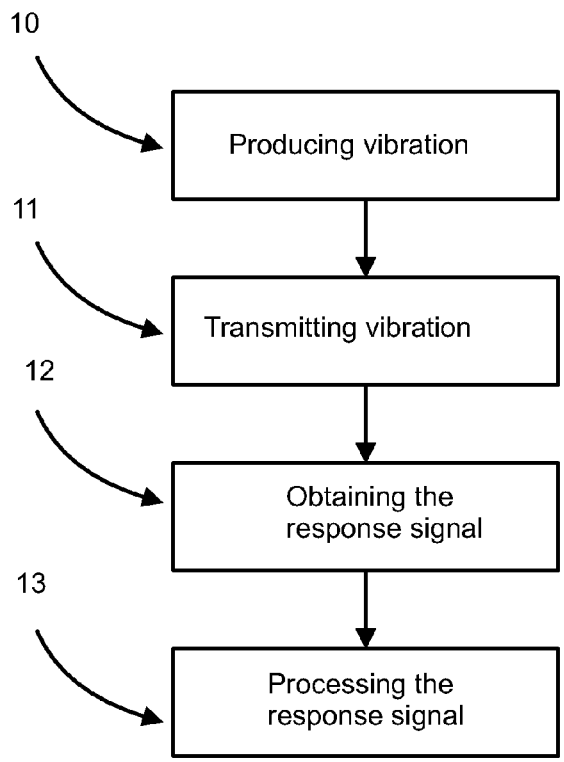
FIG. 1 shows flow chart of carrying out measurement of vibration transmittance of a sternum noninvasively.

In the following, several embodiments of the invention will be described in the context of defining sternal instability of the breastbone or abnormal healing in the sternum after open chest surgery. It is to be noted, however, that the invention is not limited to example measurement positions or measuring times with relation to performance of sternal incision. In fact, the different embodiments have applications widely in any environment or time where noninvasive vibration transmittance of a sternum is required. It should also be noted that the vibration measurement of sternum is not a diagnostic method, it gives measurement data for surgeons and doctors to be used for understanding state of patients The median sternal incision is a discontinuity in the bony structure that is made on purpose, by cutting with a saw or a like. There are normally no extra bone fragments around the incision and the bone is separated into two more or less similar halves. The place and geometry of the discontinuity are generally known and defined, though unwanted paramedian sternotomies are not uncommon. The incision is a longitudinal fault in a flat bone. Lateral sternal separation can be very prominent, in the order of millimeters or even over a centimeter. Such condition could lead to considerable changes in the transmission of vibration.

A measurement method for measuring vibration transmittance of a sternum noninvasively may comprise producing vibration, transmitting the vibration to a first side of the sternum through skin and soft tissue, obtaining response data of the sternum from a second side of the sternum through skin and soft tissue, wherein the first and the second sides of the sternum are on opposite sides of the midline of the sternum, and processing the said response data for determining transmittance of vibration of the sternum.

The measurement system for measuring vibration transmittance of a sternum noninvasively may at least comprise a device comprising a processor and a memory including computer program code for generating controlled vibration, a transmitter for providing the vibration to the tissue and to the bone underneath the tissue through skin, a sensor for obtaining the response of the bone and wherein the device is further arranged to process said response data for determining transmittance of vibration of the sternum. The measurement dynamic range may be sufficiently wide to allow high sensitivity acquisition of the weak vibration signals while excluding any larger displacements and DC offset. The frequency response of the system may cover a band at least 1000 Hz wide.

Bone properties may be estimated from measured data using models, approximations and reference measurements. Pronounced defects in the structure of bone, such as fractures, may be reflected in the measured response. For instance, there may be a considerable shift of natural resonant frequencies towards lower bands in fractured bones.

When measuring sternal instability, reference data may be obtained from the intact sternum preoperatively. Series of measurements may be performed later after sternal incision at different stages of healing. Additional relevant information, such as thickness of soft tissues at different levels of the sternum, can be obtained from other diagnostic methods such as ultrasound imaging and CT. However, it may also be possible to use simultaneous data as a reference data, but the results may not be so reliable.

FIG. 1 shows a flow chart carrying out a noninvasive defining process of instability or abnormal healing in the sternum after median sternotomy or vibration transmittance of the sternum according to an example embodiment. In stage 10 vibration with spectral content in a range, for example, 50-1500 Hz or 50-2000 Hz, is produced and transmitted to the sternum by an actuator, for example by an electromagnetic actuator or a vibration motor. In stage 11, vibration is transmitted through the skin and soft tissues to the underlying cartilage and bone, where it propagates with less attenuation. The response of the sternum is picked up, obtained, by an accelerometer, a sensor, in stage 12 and recorded in digital format. In stage 13, the obtained signal is processed by a computer, for example, by a specific device of the measuring system or by a personal computer. When processing, the mechanical transfer function of the sternum may be estimated and several descriptive parameters extracted from it. Their distributions may be defined to determine how they reflect changes occurring in the sternum.

Figure 2:
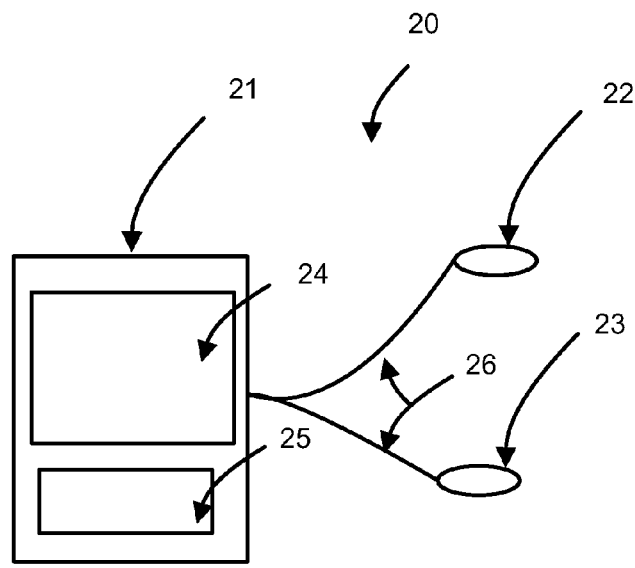
FIG. 2 shows an example of a system for measuring sternal vibration transmittance of a sternum noninvasively.

FIG. 2 shows a block diagram of the measurement system 20 according to an example embodiment. The measurement system 20 comprises at least the following functional blocks: a measurement device 21 providing interfaces for all sensors and actuators; a sensor module, an accelerometer, 22 with the circuits necessary for its operation; and a vibration source, an actuator, 23 such as a vibration motor or coil-magnet actuator.

The device 21 comprises a microcontroller 24 and at least one data storage unit 25, i.e. computer readable memory, but it may further comprise a battery pack for power supply and an optical optically isolated interface. The device 21 may also comprise user control, indicator, display and connectors. The vibration source (transmitter) 23 and sensor module (sensor) 22 are connected to the device 21, for example, by cables 26, for example, by cables terminated with standard connectors or wirelessly.

The device 21 may be based on a specially built embedded system. Its main unit may be, for example, an 8-bit microcontroller 24. Several of its integrated peripheral features may be used, such as the multi-channel analog-to-digital converter (ADC), timers, universal asynchronous transmitter-receiver (UART) and pulse width modulation (PWM) modules.

The vibration sources may be driven using power transistors. The power transistors may be driven by specialized integrated circuits to ensure proper operating mode. This measurement device may be a completely independent unit or it may operate together with a personal computer or a server.

Vibration sources may be, for example, an electromagnetic actuator, a small shaftless vibration motor, piezoelectric plates, electromechanical buzzers or small loudspeakers. However, some of the above mentioned vibration sources may be too weak and unable to overcome the considerable damping effect of soft tissues and some may not be able to provide adequate mechanical coupling or may have awkward shapes and sizes. The electromagnetic actuator consisting of permanent magnet and coil was unexpectedly found to be the preferable choice for a vibration source, even if, it may be bigger and heavier than, for example, the shaftless vibration motor, and thus may not be an obvious choice for a portable measuring system, for example, in any clinical environment.

The electromagnetic actuator may be driven by wideband signals and thus it may excite a wide range of frequencies, unlike the vibration motor which produces narrowband excitation. Wideband excitation may be used for transfer function estimation. Wideband driving signals for the electromagnetic actuator may include square or sinusoidal waveforms of linearly or nonlinearly varying frequency or spectrally uniform white noise. In addition, the use of electromagnetic actuator may lead to more consistent measurements. It should also be noted that the electromagnetic actuator may not be attached to the patient, whereas the vibration motor has to be attached, for example, by tape. So the electromagnetic actuator is easier to use clinically. In addition, both the frequency and magnitude of the vibration produced by the electromagnetic actuator may be adjusted independently. That cannot be done with the vibration motor, where there is dependence between vibration frequency and magnitude.

In the electromagnetic actuator a strong permanent magnet may be placed in close proximity to a coil, which is driven with electrical impulses. The varying magnetic field produced by the coil causes deflection of the magnet, which has sufficient mass to transmit this vibration to the bone by overcoming the damping effects of soft tissues. Vibration with the same frequency as the applied current is produced. The magnet may be loosely attached to the construction supporting the coil using a spring. This spring provides constant preload and it is possible to use this actuator without fixing it on the patient.

Vibration motors are commonly used for silent alarms in mobile phones and paging devices. It is a small direct current, DC, electromechanical drive which produces nearly sinusoidal vibration, resulting from rotation of an asymmetric load attached to the shaft.

The use of accelerometers as a vibration sensor instead of, for example, electric microphones greatly improves the performance of vibration measurement systems. Accelerometers are more robust and less sensitive to external sources of noise. However, the microphone is a conventional selection to be used as a vibration sensor.

For receiving reliable definition of the state of the sternum, the vibration measurement may be done at least twice, once before open chest operation and secondly after the operation. However, it may result in more reliable results if the measuring is repeated more than once after the operation. This way, it is possible to follow the healing process of the sternum. It is possible, for example, carry out three, four or five or more measurement sessions for each open chest operation patient. The first session may be carried out one day before the operation, the second session on the fourth postoperative day and the following sessions three weeks (21±3 days) and three months (90±10 days) postoperatively.

It is possible to use, for example, three positions for vibration stimulation and vibration sensing. It is preferred that places are anatomically well definable and easy to locate. The uppermost site may be the head of the clavicles, which articulate with the manubrium by the sternoclavicular joints. The middle location may be defined as the area above the third costal cartilage. The lowest position may be defined as the area above the fifth costal cartilage. These points may be manually identified and marked before the placement of the actuator and sensor. However, it may also be possible to use other locations or only one location when defining sternal instability.

It is also possible to connect the actuator and sensor together for measuring purpose, for example, by an arc-shaped haft or handle, so that the distance of the actuator and the sensor remains constant during recording. Suitable material for haft may be, for example, plastic. Constant distance between the actuator and the sensor may make their right placing for measuring easier. The haft may also have other shape than arc, it may be, for example, rectangular or any other shape suitable to connect the actuator and the sensor. The actuator and the sensor may be releasable from the haft.

Figure 3:
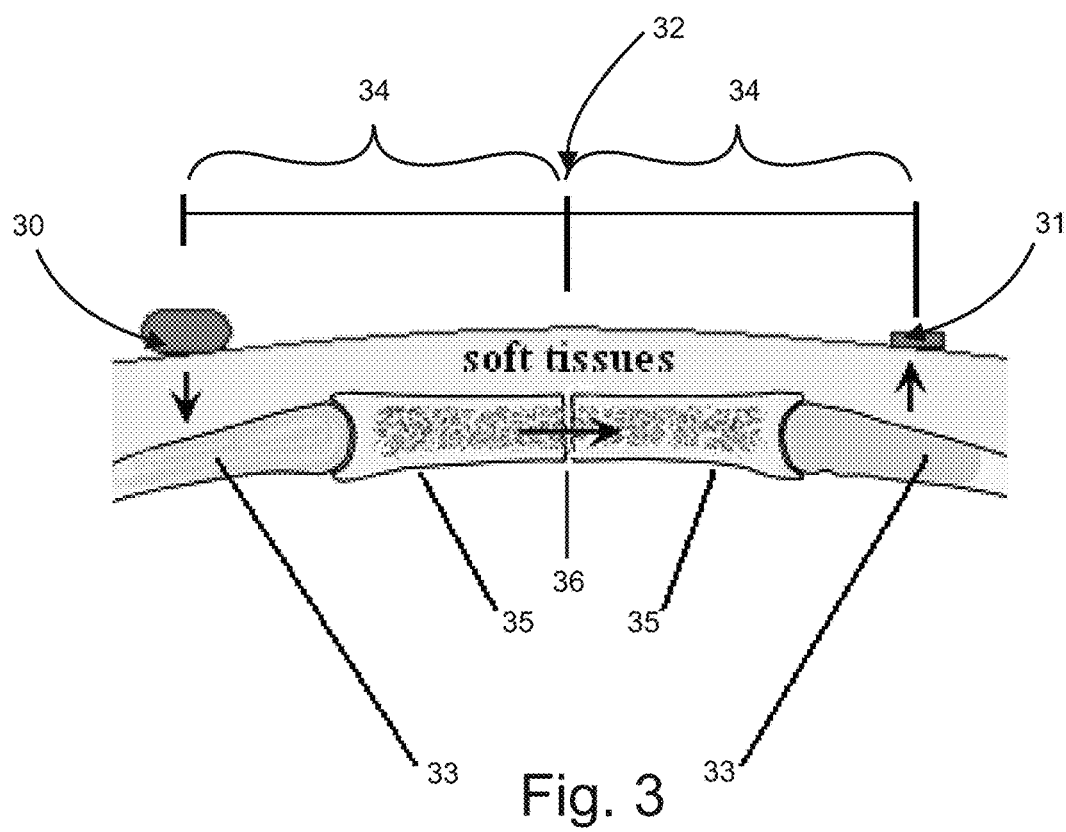
FIG. 3 shows an example of placement of an actuator and a sensor with respect to the midline according to an example embodiment.

FIG. 3 shows placement of an actuator 30 and a sensor 31 with respect to the midline 32 according to an example embodiment. Transmission of vibration i.e. stimulation through the sternal incision 36 by the actuator 30 may be applied at a distance 34 of few centimeters, for example, 2, 3, 4 or 5 centimeters, laterally to the right of the midline 32. In this example embodiment the distance is 3 cm. Acquisition i.e. signal recording by the sensor 31 may also be done at the same distance from the midline 32, but laterally to the left of the midline 32. Stimulation and acquisition are performed above costal cartilages 33 of sternal halves 35, at the middle and lower measurement positions. In the upper position stimulation and recording may be done on the heads of clavicles. However, it is also possible to stimulate from the left side of the midline 32 and to record the signal from the right side. Stimulation and recording may be done in one transversal plane, in all three positions. However, it may also be possible use other planes.

All measurements may be taken on patients in supine position. This ensures that muscles are relaxed and there is no tension or movement that could cause undesirable interference.

The measurement system may be arranged to produce controlled vibration with spectral content in the 50-1500 Hz range. Wideband vibration excitation may be produced by an electromagnetic actuator consisting of a permanent magnet placed inside a coil generating a varying magnetic field. The magnet is supported by a spring, which also provides preload when the actuator is positioned on the patient. The coil is driven by rectangular pulses of constant voltage and linearly increasing frequency in the range of approximately 50-1500 Hz.

The response of the sternum may be picked up by an accelerometer at three levels of the sternum, recorded in digital format and processed on a device. The device may be a specific device for this purpose, a personal computer or any other device suitable for this purpose. The mechanical transfer function of the sternum may be estimated and several descriptive parameters may be extracted from it. Their distributions may be defined to determine how they reflect changes occurring in the bone.

The most informative parameter for the sternal healing may be the P600-1500 index, which reflects transmittance in the wide frequency band between 600 and 1500 Hz. The P600-1500 index dropped to low level in the early postoperative period indicating the decrease in transmission. The sequence of postoperative measurements may reveal a reverse trend in the same parameter, which may be attributed to healing.

Vibration may be transmitted noninvasively through the skin and soft tissues to the underlying cartilage and bone, where it propagates with less attenuation. The sensor module picking up the response may be based on an integrated accelerometer, for example, a single-chip micro electromechanical systems (MEMS) accelerometer. The actuator and/ or the detector may be pressed against the soft tissue to enhance transmittance of vibration between the device and the tissue.

The response picked up by an accelerometer, for example, at three levels of the sternum, and recorded in digital format may be processed on a measuring device or a computer such as a personal computer. The device that processes the response data may be called as a computing device. It is also possible, for example, that the device 21 transmits the response data to the computer acting as a computing device instead of the device 21. Then the computer processes the response data. The mechanical transfer function of the sternum may be estimated from the recorded data.

Figure 4:
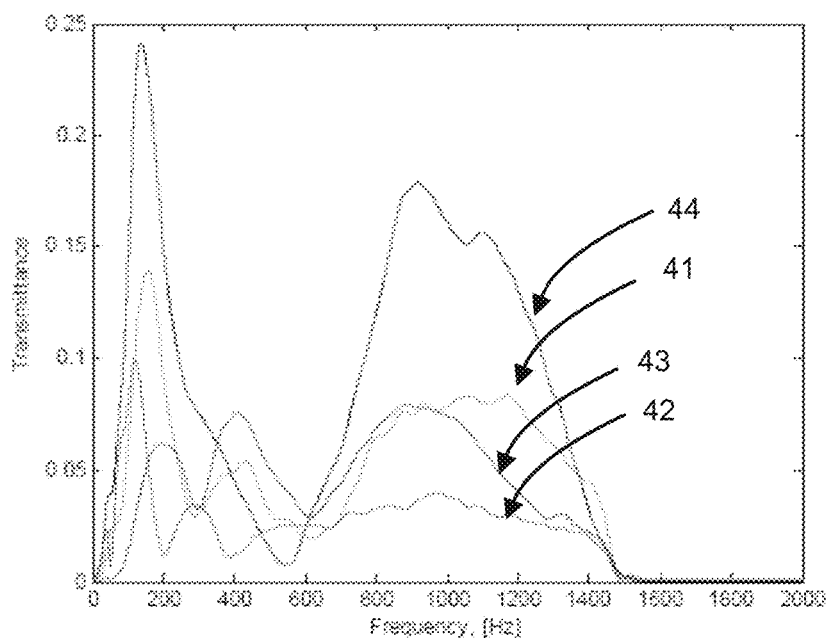
FIG. 4 shows an example of transfer functions deduced from obtained data of the sternum of one measuring position for a single patient according to an example embodiment.

Transfer functions obtained from recorded digital data of the sternum of one measuring position for a single patient are shown in FIG. 4. It contains four curves, corresponding to four measurement session. Curve 41 corresponds a transfer function obtained from a preoperative measurement. Curve 42 corresponds a transfer function of measuring that has been measured in the early postoperative period after an open chest operation, for example, 3 days after the operation. Curve 43 corresponds a transfer function from a measurement that has been obtained, for example, 3 weeks after the operation and curve 44 corresponds a transfer function of measuring that has been measured, for example, 3 months. These measurement times are just an example of possible measurement times, they can be selected differently.

Figure 5:
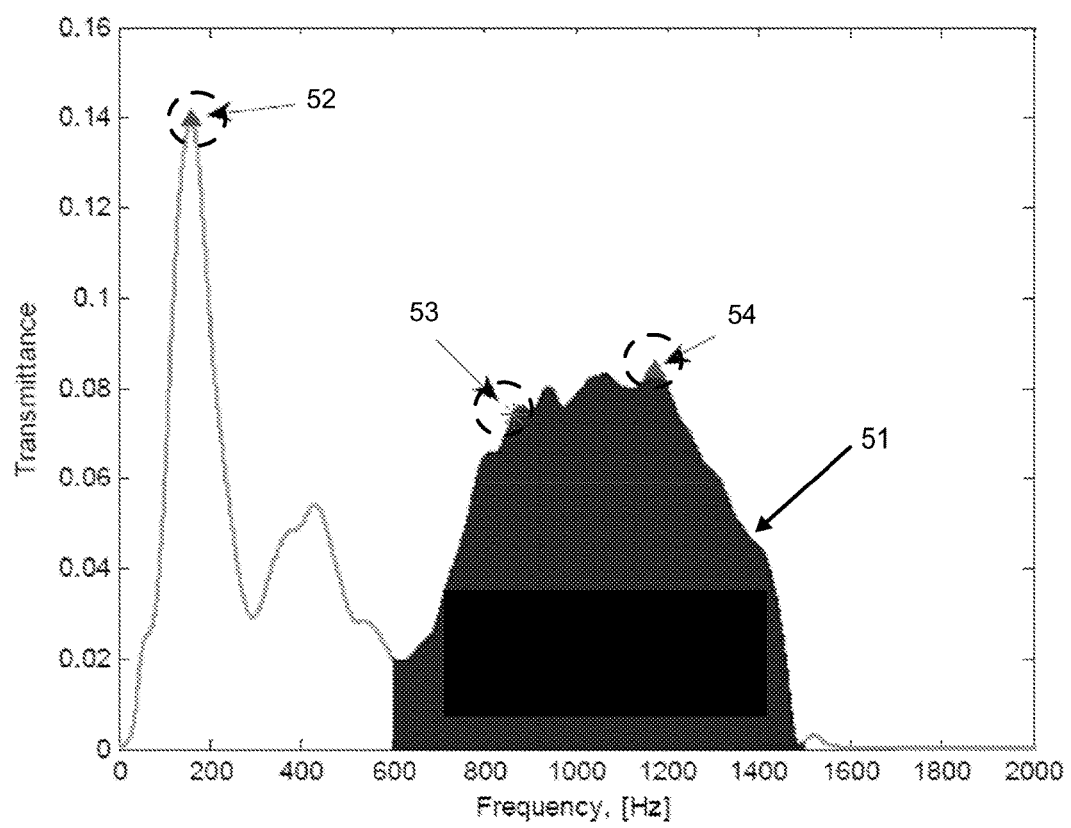
FIG. 5 shows an example of several descriptive parameters that may be extracted from a mechanical transfer function.

Several descriptive parameters may be extracted from the mechanical transfer function. On the base of the extracted parameters it is possible to determine changes occurring in the bone of the sternum. Parameters to be used for determination of the sternal healing may be, for example, P600-1500 index, which reflects transmittance in the wide frequency band between 600 and 1500 Hz. The P600-1500 index drops to low level in the early postoperative period indicating a decrease in transmission. The sequence of postoperative measurements may reveal a reverse trend in the same parameter, which may attribute to healing. Several descriptive parameters that are extracted from the estimated mechanical transfer functions are disclosed in FIG. 5. They include magnitudes and frequencies of various peaks, as well as more general indices that cover wider frequency bands. The P600-1500 index represents the integrated transmittance within a wide band in the higher frequency range. This index was normalized with respect to the total integrated transmittance (Ptotal), yielding the so-called P600-1500/Ptotal index 51. In FIG. 5 the P600-1500/Ptotal index is 0.6342. Also main peak in 50-600 Hz band 52 (in FIG. 5 the frequency is 158 Hz and the magnitude 0.1394), median frequency 53 (864 Hz in FIG. 5) and main peak in 600-1500 Hz band 54 (in FIG. 5 the frequency is 1173 Hz and the magnitude 0.0839) are parameters that may be determined from the measured transfer function.

Instead of presenting the absolute values of parameters, it may be sometimes more informative to show how the parameters change between measurements. For this reason, a simple metric called relative difference may be used.

The various embodiments of the invention can be implemented with the help of computer program code that resides in a memory and causes the relevant apparatuses to carry out the invention. For example, a measuring device acting as a terminal device may comprise circuitry and electronics for handling, receiving and transmitting data, computer program code in a memory, and a processor that, when running the computer program code, causes the terminal device to carry out the features of an embodiment.

It is obvious that the present invention is not limited solely to the above-presented embodiments, but it can be modified within the scope of the appended claims.

The invention claimed is:

1. A method for measuring vibration transmittance of a sternum noninvasively with an apparatus, comprising:
   producing vibration with spectral content,
   transmitting the vibration with spectral content with varying frequency to a first side of the sternum through skin and soft tissues by a transmitter,
   obtaining response data of the sternum from a second side of the sternum through skin and soft tissues by an accelerometer, which first and second sides of the sternum are on different sides of the midline of the sternum, and wherein there is a handle between the transmitter and the accelerometer, so that the distance of the transmitter and the accelerometer remains at a constant distance within 2 to 5 centimeters from the midline of the sternum during measuring, and
   processing said response data for determining integrated transmittance of vibration of the sternum.

2. A method according to claim 1, wherein spectral content of the produced vibration is in the 50-1500 Hz range.

3. A method according to claim 1, wherein spectral content of the produced vibration is in the 50-2000 Hz range.

4. A method according to claim 1, wherein the processing comprises producing a transfer function from response data and extracting parameters from the transfer function.

5. A method according to claim 1, wherein the measuring of vibration transmittance of the sternum is performed at least twice, wherein the first measuring is executed before a sternal incision of the sternum and the second measuring is executed after the sternal incision of the sternum, and wherein the response data of the first and second measurements are compared.

6. A method according to claim 1, wherein the measuring of vibration transmittance of the sternum is executed to the sternum at least at two different positions.

7. A system for measuring vibration transmittance of a sternum noninvasively, wherein the system comprises a device comprising a processor and a memory including computer program code for producing vibration, a transmitter for transmitting the vibration with spectral content with varying frequency to a first side of the sternum through skin and soft tissues, by an accelerometer for obtaining response data of the sternum from a second side of the sternum through skin and soft tissues, which first and second sides of the sternum are on different sides of the midline of the sternum, and wherein there is a handle between the transmitter and the accelerometer, so that the distance of the transmitter and the accelerometer remains at a constant distance within 2 to 5 centimeters from the midline of the sternum during measuring, and wherein the device is further arranged to process said response data for determining integrated transmittance of vibration of the sternum.

8. A system according to claim 7, wherein the device is further arranged to receive said obtained data for further data processing.

9. A system according to claim 7, wherein the device is connected to a computer that is arranged to receive said obtained data for further data processing.

10. A system according to claim 7, wherein the transmitter is an electromagnetic actuator.

11. A device for measuring sternal vibration transmittance of a sternum noninvasively, wherein the device comprises:

a measurement device comprising a processor and a memory including computer program code for generating vibration with spectral content, a transmitter for transmitting the vibration with spectral content with varying frequency to a first side of the sternum through skin and soft tissue, an accelerometer for obtaining response data of the sternum from a second side of the sternum through skin and soft tissue, which first and second sides of the sternum are on different sides of the midline of the sternum, and wherein there is a handle between the transmitter and the accelerometer, so that the distance of the transmitter and the accelerometer remains at a constant distance within 2 to 5 centimeters from the midline of the sternum during measuring, and a computing device for processing said response data for determining integrated transmittance of vibration of the sternum.

12. A device according to a claim 11, wherein the transmitter is an electromagnetic actuator.

13. A device according to claim 11, wherein spectral content of the produced vibration is in the 50-1500 Hz range.

14. A device according to claim 11, wherein spectral content of the produced vibration is in the 50-2000 Hz range.

15. A device according to claim 11, wherein the processing comprises producing a transfer function from response data and extracting parameters from the transfer function.

16. A device according to claim 11, wherein the computing device is the measurement device.

17. A device according to claim 11, wherein the computing device is a computer receiving the response data from the measurement device.

* * * * *